US008384027B2

(12) United States Patent
Hoyes et al.

(10) Patent No.: US 8,384,027 B2
(45) Date of Patent: Feb. 26, 2013

(54) ION GUIDE ARRAY (75) Inventors: John B. Hoyes, Cheshire (GB); David Langridge, Manchester (GB)

(73) Assignee: Micromass UK Limited, Manchester (GB)

( * ) Notice: Subject to any disclaimer, the term of this patent is extended or adjusted under 35 U.S.C. 154(b) by 0 days.

(21) Appl. No.: 13/119,264

(22) PCT Filed: Sep. 17, 2009

(86) PCT No.: PCT/GB2009/002232
§ 371 (c)(1),
(2), (4) Date: May 17, 2011

(87) PCT Pub. No.: WO2010/032015
PCT Pub. Date: Mar. 25, 2010

(65) Prior Publication Data
US 2011/0266435 A1    Nov. 3, 2011

Related U.S. Application Data (60) Provisional application No. 61/100,025, filed on Sep. 25, 2008.

(30) Foreign Application Priority Data

Sep. 18, 2008 (GB) .................................. 0817115.9

(51) Int. Cl.
H01J 49/42 (2006.01)
(52) U.S. Cl. ........................................ 250/292; 250/285
(58) Field of Classification Search .......... 250/281–283, 250/285, 290–293
See application file for complete search history.

(56) References Cited

U.S. PATENT DOCUMENTS

| 5,420,425 | A | * | 5/1995 | Bier et al. ...................... 250/292 |
| 5,576,540 | A | | 11/1996 | Jolliffe |
| 6,121,607 | A | * | 9/2000 | Whitehouse et al. .......... 250/288 |
| 6,403,952 | B2 | * | 6/2002 | Whitehouse et al. .......... 250/288 |
| 6,417,511 | B1 | * | 7/2002 | Russ et al. ...................... 250/292 |
| 6,914,241 | B2 | | 7/2005 | Giles et al. |
| 7,982,183 | B2 | * | 7/2011 | Makarov et al. ............... 250/283 |
| 2002/0063210 | A1 | | 5/2002 | Bateman et al. |
| 2004/0135080 | A1 | | 7/2004 | Ouyang et al. |
| 2007/0045533 | A1 | | 3/2007 | Krutchinsky et al. |
| 2009/0173877 | A1 | * | 7/2009 | Bateman et al. ............... 250/282 |
| 2011/0057097 | A1 | * | 3/2011 | Bateman et al. ............... 250/283 |

FOREIGN PATENT DOCUMENTS

| GB | 2421845 | 7/2006 |
| GB | 2441198 | 2/2008 |
| GB | 2447330 | 9/2008 |
| GB | 2455171 | 3/2009 |
| GB | 2457556 | 8/2009 |
| WO | 2007066114 | 6/2007 |

OTHER PUBLICATIONS

Search and Examinatoin Report for Application No. GB0916355.1, dated Jun. 14, 2011.

(Continued)

Primary Examiner — Bernard E Souw
(74) Attorney, Agent, or Firm — Diederiks & Whitelaw, PLC (57) ABSTRACT An ion guide array is disclosed comprising a first ion guide section and a second ion guide section and optionally further ion guide sections. Each ion guide section may comprise a plurality of electrodes having an aperture through which ions are transmitted in use. A transfer section is arranged at the exit of the first ion guide section and ions are transmitted radially from the first ion guide section into the second ion guide section. The electrodes in the transfer section may have a radial aperture enabling ions to be transmitted radially from the first ion guide section to the second ion guide section.

15 Claims, 4 Drawing Sheets

OTHER PUBLICATIONS

Search and Examination Report for Application No. GB0916355.1, dated Feb. 17, 2010.
Search and Examination Report for Application No. GB1019991.7, dated Jun. 14, 2011.
Search and Examination Report for Application No. GB1019992.5, dated Jun. 14, 2011.

* cited by examiner

ION GUIDE ARRAY

CROSS REFERENCE TO RELATED APPLICATION

This application is the National Stage of International Application No. PCT/GB2009/002232, filed on Sep. 17, 2009 and designating the United States, which claims benefit of a priority to U.S. Provisional Patent Application No. 61/100,025, filed on Sep. 25, 2008 and United Kingdom Priority Application No. 0817115.9, filed Sep. 18, 2008. The contents of these applications are expressly incorporated herein by reference in their entirety.

BACKGROUND OF THE INVENTION

The present invention relates to an ion guide, an ion mobility spectrometer or separator, a mass spectrometer, a method of guiding ions, a method of separating ions according to their ion mobility and a method of mass spectrometry.

The analytical utility of providing a forward impetus for ions confined by RF fields in the presence of gaseous media has long been understood. Particular applications include the creation of collision cells for tandem mass spectrometers wherein fast transit times are desirable e.g. when performing MRM, parent ion scanning or neutral loss experiments on triple quadrupole instruments. Such devices may also be used to separate ions according to their ion mobility and these are finding wider use in hybrid ion mobility-mass spectrometer instruments. Typical pressure ranges of operation are in the region of 0.001 to 10 mbar.

Various ion guides are known including an ion tunnel ion guide comprising a plurality of ring electrodes. Opposite phases of an RF voltage are applied to adjacent electrodes so that ions are confined by a pseudo-potential well within the ion tunnel ion guide. A DC travelling wave may be applied to the ring electrodes in order to urge ions along the length of the ion guide. Ions are transmitted and guided along the length of the ion guide passing through the apertures in the ring electrodes. It is also known to provide an ion mobility spectrometer comprising an ion tunnel ion guide maintained at a relatively high pressure. As ions are transmitted through the ion tunnel ion guide, the ions become separated temporally according to their ion mobility.

U.S. Pat. No. 6,914,241 (Giles) describes how ions may be separated according to their ion mobility by progressively applying transient DC voltages along the length of an RF ion guide or ion mobility separator comprising a plurality of electrodes. The ion mobility separator may comprise an AC or RF ion guide such as a multipole rod set or a stacked ring set. The ion guide is segmented in the axial direction so that independent transient DC potentials can be applied to each segment. The transient DC potentials are superimposed on top of an AC or RF voltage (which acts to confine ions radially) and/or any constant DC offset voltage. The transient DC potentials generate a travelling wave which moves along the axial direction and translates ions along the ion mobility separator.

A known ion mobility separation device comprises a drift tube comprising a series of rings wherein a constant potential difference is maintained between adjacent members such that a constant electric field is produced. A pulse of ions is introduced into the drift tube which contains a buffer gas and ions separate along the longitudinal axis according to their ion mobility. These devices are operable at atmospheric pressure without RF confinement and can offer resolutions up to 150 (Wu et. A. Anal. Chem. 1988, 70, 4929-4938). Operation at lower pressures more suitable for hybrid ion mobility-mass spectrometer instruments leads to greater diffusion losses and lower resolution. An RF pseudo-potential well may be arranged to confine ions radially and may be used to transportions efficiently by acting as an ion guide and so solving the problem of diffusion losses. Ions may be propelled along the guide and ions may be separated according to their ion mobility. However, the problem of the lower pressure of operation of mobility separation is that in order to achieve a high resolution of mobility separation, a relatively long drift tube must be employed in order to keep within the low field limit as described in more detail below.

In order to separate ions according to their mobility in an RF ion guide a DC electric field must be generated which is orthogonal to the RF radial confinement. If a constant electric field E is applied to drive the ions through the ion guide containing a gas then the ion will acquire a characteristic velocity:

$$v_d = E \cdot K \qquad (1)$$

wherein K is the ion mobility.

To achieve a mobility separation whereby the ions acquire negligible energy compared to the background thermal energy of a gas it is necessary to consider the parameter E/P, wherein P is the pressure of the neutral gas.

To maintain mobility separation in the so called low field regime whereby ions do not receive kinetic energy from the driving field it is required that the parameter E/P is less than about 2V/cm-mbar.

Under low field conditions in a drift tube of length L and applied voltage drop V the resolution is found to be independent of ion mobility and only dependent on the voltage drop such that in the absence of space charge effects:

$$\frac{L}{|\bar{x}|} = \frac{\sqrt{V}}{0.173} \qquad (2)$$

wherein $|\bar{x}|$ is the mean displacement of the centre of mass of the moving ion cloud.

The parameter $$\frac{L}{|\bar{x}|}$$

is effectively the resolution of the mobility separation so it can be seen that the performance of the spectrometer can be increased by maintaining larger voltage drops across the drift tube. In hybrid ion mobility-mass spectrometer instruments the typical pressure of the ion mobility drift region is 0.5-1 mbar. Operating at pressures much greater than this puts great demands upon the vacuum system which needs to be differentially pumped in order for the mass spectrometer stages to operate efficiently.

At a typical drift tube length of 20 cm and operating pressure of 0.5 mbar the maximum voltage that can be applied within the low field limit is 20 V giving a maximum resolution of 26. To achieve a resolution of 100 under the same conditions would require a drift tube length of over 3 meters which is impractical for commercial instruments.

It is desired to provide an improved ion guide and ion mobility spectrometer.

SUMMARY OF THE INVENTION

According to an aspect of the present invention there is provided an ion guide comprising:

a first ion guide section comprising a first plurality of electrodes having at least one aperture through which ions are transmitted in use;

a second ion guide section comprising a second plurality of electrodes having at least one aperture through which ions are transmitted in use; and a first transfer section connecting the first ion guide section with the second ion guide section wherein ions are transmitted radially, in use, in the first transfer section from the first ion guide section into the second ion guide section.

The first transfer section preferably comprises one or more electrodes in the first ion guide section having a first radial aperture or cut-out and one or more electrodes in the second ion guide section having a second radial aperture or cut-out. The first radial aperture or cut-out and the second radial aperture or cut-out are preferably substantially aligned. The first radial aperture or cut-out preferably faces the second radial aperture or cut-out.

The ion guide preferably further comprises a first device for urging ions from the first ion guide section into the second ion guide section via the first transfer section. The first device preferably comprises: (i) a device for maintaining a DC potential bias across the first transfer section so that ions are urged from the first ion guide section into the second ion guide section; and/or (ii) a device for applying one or more transient DC voltages or potentials or one or more transient DC voltage or potential waveforms to electrodes arranged in the first transfer section so that ions are urged from the first ion guide section into the second ion guide section.

According to the preferred embodiment ions are transmitted in use in a first direction through the first ion guide section and in a second direction through the second ion guide section, wherein either: (i) the first direction is substantially the same as the second direction; or (ii) the first direction is substantially different to or counter to the second direction.

According to an embodiment of the present invention one or more transfer sections may be provided wherein one or more electrodes in an ion guide section comprise two or more radial apertures or cut-outs. In a first mode of operation ions may be transmitted in a first radial direction from one ion guide section to another ion guide section. In a second mode of operation ions may be transmitted in a second radial direction which is different to or opposed to said first radial direction from one ion guide section to another ion guide section. Another embodiment is contemplated wherein ions may be transferred in a split manner so that some ions are transmitted in a first radial direction whereas some others ions are simultaneously transmitted in a second different radial direction.

The ion guide preferably further comprises a first transient DC voltage means arranged and adapted to apply one or more transient DC voltages or potentials or one or more transient DC voltage or potential waveforms to at least some of the first plurality of electrodes in order to urge, force, drive or propel at least some ions along at least 5%, 10%, 15%, 20%, 25%, 30%, 35%, 40%, 45%, 50%, 55%, 60%, 65%, 70%, 75%, 80%, 85%, 90%, 95% or 100% of the length of the first ion guide section.

The ion guide preferably further comprises a second transient DC voltage means arranged and adapted to apply one or more transient DC voltages or potentials or one or more transient DC voltage or potential waveforms to at least some of the second plurality of electrodes in order to urge, force, drive or propel at least some ions along at least 5%, 10%, 15%, 20%, 25%, 30%, 35%, 40%, 45%, 50%, 55%, 60%, 65%, 70%, 75%, 80%, 85%, 90%, 95% or 100% of the length of the second ion guide section.

The ion guide preferably further comprises a third ion guide section comprising a third plurality of electrodes having at least one aperture through which ions are transmitted in use.

The ion guide preferably further comprises a second transfer section connecting the second ion guide section with the third ion guide section wherein ions are transmitted radially in the second transfer section from the second ion guide section into the third ion guide section. The second transfer section preferably comprises one or more electrodes in the second ion guide section having a third radial aperture or cut-out and one or more electrodes in the third ion guide section having a fourth radial aperture or cut-out.

According to the preferred embodiment the third radial aperture or cut-out and the fourth radial aperture or cut-out are substantially aligned. The third radial aperture or cut-out preferably faces the fourth radial aperture or cut-out.

The ion guide preferably further comprises a second device for urging ions from the second ion guide section into the third ion guide section via the second transfer section. The second device preferably comprises: (i) a device for maintaining a DC potential bias across the second transfer section so that ions are urged from the second ion guide section into the third ion guide section; and/or (ii) a device for applying one or more transient DC voltages or potentials or one or more transient DC voltage or potential waveforms to electrodes arranged in the second transfer section so that ions are urged from the second ion guide section into the third ion guide section.

According to an embodiment ions are transmitted in use in a third direction through the third ion guide section and wherein either: (i) the third direction is substantially the same as the first direction and/or the second direction; or (ii) the third direction is substantially different to or counter to the first direction and/or the second direction.

The ion guide preferably further comprises a third transient DC voltage means arranged and adapted to apply one or more transient DC voltages or potentials or one or more transient DC voltage or potential waveforms to at least some of the third plurality of electrodes in order to urge, force, drive or propel at least some ions along at least 5%, 10%, 15%, 20%, 25%, 30%, 35%, 40%, 45%, 50%, 55%, 60%, 65%, 70%, 75%, 80%, 85%, 90%, 95% or 100% of the length of the third ion guide section.

The ion guide preferably comprises an entrance region, a central region and an exit region and wherein the entrance region and/or the central region and/or the exit region is maintained in use at a pressure selected from the group consisting of: (i) >100 mbar; (ii) >10 mbar; (iii) >1 mbar; (iv) >0.1 mbar; (v) >$10^{-2}$ mbar; (vi) >$10^{-3}$ mbar; (vii) >$10^{-4}$ mbar; (viii) >$10^{-5}$ mbar; (ix) >$10^{-6}$ mbar; (x) <100 mbar; (xi) <10 mbar; (xii) <1 mbar; (xiii) <0.1 mbar; (xiv) <$10^{-2}$ mbar; (xv) <$10^{-3}$ mbar; (xvi) <$10^{-4}$ mbar; (xvii) <$10^{-5}$ mbar; (xviii) <$10^{-6}$ mbar; (xix) 10-100 mbar; (xx) 1-10 mbar; (xxi) 0.1-1 mbar; (xxii) $10^{-2}$ to $10^{-1}$ mbar; (xxiii) $10^{-3}$ to $10^{-2}$ mbar; (xxiv) $10^{-4}$ to $10^{-3}$ mbar; and (xxv) $10^{-5}$ to $10^{4}$ mbar.

According to an embodiment in a first mode of operation ions are arranged to pass through the first ion guide section and to exit the first ion guide section without being transmitted into the second ion guide section and wherein in a second mode of operation ions are arranged to pass through the first ion guide section and to be transferred radially from the first ion guide section to the second ion guide section.

According to an embodiment:

(i) in a first mode of operation ions are arranged to travel through the ion guide along a first ion path having a first ion path length before exiting the ion guide and wherein in a second mode of operation ions are arranged to travel through the ion guide along a second ion path having a second ion path length before exiting the ion guide, wherein the ratio of the second ion path length to the first ion path length is at least 1.5, 2, 2.5, 3, 3.5, 4, 4.5, 5, 5.5, 6, 6.5, 7, 7.5, 8, 8.5, 9, 9.5 or 10; and/or (ii) in a mode of operation the ion guide forms a closed loop or circuit and wherein at least some ions are arranged to make one or more circuits of the ion guide; and/or (iii) in a mode of operation ions having a first ion mobility or mass to charge ratio are arranged to exit the ion guide via a first ion exit and ions having a second ion mobility or mass to charge ratio are arranged to exit the ion guide via a second different ion exit.

According to an embodiment the ion guide further comprises a device for causing gas to flow through the first ion guide section and/or the second ion guide section and/or one or more further ion guide sections. The gas is preferably arranged to flow in a direction which is generally counter or opposed to the direction in which ions are transmitted through the first ion guide section and/or the second ion guide section and/or one or more further ion guide sections.

According to another aspect of the present invention there is provided an ion guide comprising:

a first ion guide section having a first longitudinal or curved axis wherein ions are confined radially, in use, within the first ion guide section;

a second ion guide section having a second longitudinal or curved axis wherein ions are confined radially, in use, within the second ion guide section; and a transfer section comprising a portion of the first ion guide section and a portion of the second ion guide section wherein ions are transferred, in use, from the first ion guide section into the second ion guide section at an angle θ measured with respect to the first axis, wherein θ>60°.

The first ion guide section preferably comprises either: (i) an ion tunnel or ion funnel ion guide; (ii) a multipole rod set ion guide; (iii) an axially segmented multipole rod set ion guide; or (iv) a plurality of plate electrodes arranged generally in the plane of ion travel.

The second ion guide section preferably comprises either: (i) an ion tunnel or ion funnel ion guide; (ii) a multipole rod set ion guide; (iii) an axially segmented multipole rod set ion guide; or (iv) a plurality of plate electrodes arranged generally in the plane of ion travel.

The angle θ is preferably further selected from the group consisting of: (i) >65°; (ii) >70°; (iii) >75°; (iv) >80°; (v) >85°; or (vi) 90°.

According to another aspect of the present invention there is provided an ion mobility spectrometer or separator comprising an ion guide as described above.

According to another aspect of the present invention there is provided a collision, fragmentation or reaction cell comprising an ion guide as described above.

According to a preferred embodiment the collision, fragmentation or reaction cell comprising an ion guide as described above may comprise a Proton Transfer Reaction ("PTR") reaction and/or an Electron Transfer Dissociation ("ETD") fragmentation cell. ETD is a process wherein positively charged analyte ions are reacted with negatively charged reagent ions and wherein electrons are transferred from negatively charged reagent ions to positively charged analyte ions. After electron transfer, the charge-reduced peptide or analyte ion dissociates through the same mechanisms which are believed to be responsible for fragmentation by Electron Capture Dissociation i.e. it is believed that Electron Transfer Dissociation cleaves the amine bond in a similar manner to Electron Capture Dissociation. As a result, the product or fragment ions which are produced by Electron Transfer Dissociation of peptide analyte ions comprise mostly c-type and z-type fragment or product ions.

One particular advantage of Electron Transfer Dissociation is that such a process is particularly suited for the identification of post-translational modifications ("PTMs") since weakly bonded PTMs like phosphorylation or glycosylation will survive the electron induced fragmentation of the backbone of the amino acid chain.

According to an embodiment:

(a) in a mode of operation ions are predominantly arranged to fragment within the collision, fragmentation or reaction cell by Collision Induced Dissociation to form product or fragment ions, wherein the product or fragment ions comprise a majority of b-type product or fragment ions and/or y-type product or fragment ions; and/or (b) in a mode of operation ions are predominantly arranged to fragment by Electron Transfer Dissociation within the collision, fragmentation or reaction cell to form product or fragment ions, wherein the product or fragment ions comprise a majority of c-type product or fragment ions and/or z-type product or fragment ions.

According to an embodiment in order to effect Electron Transfer Dissociation either:

(a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged (preferably basic) gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged (preferably superbase) reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

According to an embodiment the multiple charged analyte cations or positively charged ions preferably comprise peptides, polypeptides, proteins or biomolecules.

According to an embodiment in order to effect Electron Transfer Dissociation the reagent anions or negatively charged ions may be derived from a polyaromatic hydrocarbon or a substituted polyaromatic hydrocarbon. The reagent anions or negatively charged ions may be derived from a low electron affinity substrate. According to an embodiment the reagent ions may be derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone. The reagent ions or negatively charged ions may comprise azobenzene anions or azobenzene radical anions. Other embodiments are contemplated wherein the reagent ions comprise other ions, radical anions or metastable ions.

According to an embodiment in order to effect Proton Transfer Reaction protons may be transferred from one or more multiply charged analyte cations or positively charged ions to one or more reagent anions or negatively charged ions whereupon at least some of the multiply charged analyte cations or positively charged ions are preferably reduced in charge state. It is also contemplated that some of the cations may also be induced to dissociate and form product or fragment ions.

Protons may be transferred from one or more multiply charged analyte cations or positively charged ions to one or more neutral, non-ionic or uncharged reagent gases or vapours whereupon at least some of the multiply charged analyte cations or positively charged ions are preferably reduced in charge state. It is also contemplated that some of the cations may also be induced to dissociate and form product or fragment ions.

The multiply charged analyte cations or positively charged ions preferably comprise peptides, polypeptides, proteins or biomolecules.

According to an embodiment in order to effect Proton Transfer Reaction in the collision, fragmentation or reaction cell either the reagent anions or negatively charged ions may be derived from a compound selected from the group consisting of: (i) carboxylic acid; (ii) phenolic; and (iii) a compound containing alkoxide. The reagent anions or negatively charged ions may alternatively be derived from a compound selected from the group consisting of: (i) benzoic acid; (ii) perfluoro-1,3-dimethylcyclohexane or PDCH; (iii) sulphur hexafluoride or SF6; and (iv) perfluorotributylamine or PFTBA.

According to an embodiment one or more reagent gases or vapours may be provided within the collision, fragmentation or reaction cell and may comprise a superbase gas. The one or more reagent gases or vapours may be selected from the group consisting of: (i) 1,1,3,3-Tetramethylguanidine ("TMG"); (ii) 2,3,4,6,7,8,9,10-Octahydropyrimidol[1,2-a]azepine {Synonym: 1,8-Diazabicyclo[5.4.0]undec-7-ene ("DBU")}; or (iii) 7-Methyl-1,5,7-triazabicyclo[4.4.0]dec-5-ene ("MTBD") {Synonym: 1,3,4,6,7,8-Hexahydro-1-methyl-2H-pyrimido[1,2-a]pyrimidine}.

Further embodiments are contemplated wherein the same reagent ions or neutral reagent gas which is disclosed above in relation to effecting Electron Transfer Dissociation may also be used to effect Proton Transfer Reaction.

According to another aspect of the present invention there is provided a mass spectrometer comprising an ion guide as described above.

According to another aspect of the present invention there is provided a method of guiding ions comprising:

providing an ion guide comprising a first ion guide section comprising a first plurality of electrodes having at least one aperture through which ions are transmitted, a second ion guide section comprising a second plurality of electrodes having at least one aperture through which ions are transmitted and a first transfer section connecting the first ion guide section with the second ion guide section; and transmitting ions radially in the first transfer section from the first ion guide section into the second ion guide section.

According to another aspect of the present invention there is provided a method of guiding ions comprising:

providing a first ion guide section having a first longitudinal or curved axis wherein ions are confined radially within the first ion guide section and a second ion guide section having a second longitudinal or curved axis wherein ions are confined radially within the second ion guide section; and transferring ions from the first ion guide section to the second ion guide section at an angle θ measured with respect to the first axis, wherein θ>60°.

According to another aspect of the present invention there is provided a computer program executable by the control system of a mass spectrometer comprising a first ion guide section comprising a first plurality of electrodes having at least one aperture through which ions are transmitted in use, a second ion guide section comprising a second plurality of electrodes having at least one aperture through which ions are transmitted in use and a first transfer section connecting the first ion guide section with the second ion guide section, the computer program being arranged to cause the control system:

(i) to cause ions to be transmitted radially in the first transfer section from the first ion guide section into the second ion guide section.

According to another aspect of the present invention there is provided a computer readable medium comprising computer executable instructions stored on the computer readable medium, the instructions being arranged to be executable by a control system of a mass spectrometer comprising a first ion guide section comprising a first plurality of electrodes having at least one aperture through which ions are transmitted in use, a second ion guide section comprising a second plurality of electrodes having at least one aperture through which ions are transmitted in use and a first transfer section connecting the first ion guide section with the second ion guide section, the computer program being arranged to cause the control system:

(i) to cause ions to be transmitted radially in the first transfer section from the first ion guide section into the second ion guide section.

The computer readable medium is preferably selected from the group consisting of: (i) a ROM; (ii) an EAROM; (iii) an EPROM; (iv) an EEPROM; (v) a flash memory; (vi) an optical disk; (vii) a RAM; and (viii) a hard disk drive.

According to another aspect of the present invention there is provided a method of separating ions according to their ion mobility comprising:

providing a plurality of ion guide sections which in combination provide a generally folded or tortuous ion guide path so that ions are reversed in direction one or more times as the ions are transmitted along the ion guide path; and causing ions to pass in a generally radial direction when passing from an ion guide section to an adjacent ion guide section.

Ions are preferably confined radially within the plurality of ion guide sections.

The step of causing ions to pass in a generally radial direction preferably further comprises causing ions to pass through one or more radial apertures in one or more electrodes arranged at an interconnection between two ion guide sections.

According to another aspect of the present invention there is provided an ion mobility separator comprising:

a plurality of ion guide sections which in combination provide a generally folded or tortuous ion guide path wherein, in use, ions are reversed in direction one or more times as the ions are transmitted along the ion guide path; and a device for causing ions to pass in a generally radial direction when passing from an ion guide section to an adjacent ion guide section.

According to a preferred embodiment of the present invention a plurality of stacked ring ion guides ("SRIGs") are provided. Each stacked ring ion guide preferably comprises a plurality of ring or plate electrodes or electrodes having one or more apertures through which ions are transmitted in use. An AC or RF voltage is preferably applied to alternate plates or ring electrodes of the stacked ring ion guides in order to confine-ions radially within the ion guides within pseudo-potential wells. According to an embodiment alternate electrodes are preferably supplied with opposite phases of the AC or RF voltage.

Other less preferred embodiments are contemplated wherein the ion guides may comprise a multiple rod set or an axially segmented multipole rod set. A further embodiment is also contemplated wherein the ion guides may comprise a plurality of plate electrodes arranged generally in the plane of ion travel. Opposite phases of an AC or RF voltage are applied to adjacent plate electrodes in order to confine ions within the ion guides.

One or more travelling DC waves or transient DC voltages may be applied to one or more of the stacked ring ion guide plates or rings or other ion guide devices in order to drive ions through the stacked ring ion guides or other ion guides and preferably through a buffer gas. As a result, according to the preferred embodiment ions may be separated according to their ion mobility as they pass along and through one or more of the stacked ring ion guides or other ion guides.

According to an embodiment ions preferably enter a first stacked ring ion guide or other ion guide in a first axial direction and the ions preferably exit a final or last stacked ring ion guide or other ion guide in a second axial direction. The second axial direction may be the same as or different to the first axial direction. Ions may be passed between two adjacent stacked ring ion guides or other ion guides by means of localised regions at the start and/or end of each stacked ring ion guide or other ion guide. In these regions one or more adjacent stacked ring electrodes or rings or other electrodes may be arranged to have an aligned radial aperture which enables ions to be transferred from one stacked ring ion guide or other ion guide to an adjacent stacked ring ion guide or other ion guide in a radial manner.

According to a preferred embodiment a DC offset (e.g. <5 V, 5-10 V, 10-15 V or >15 V) may be maintained between two adjacent stacked ring ion guides or other ion guides in order to the transfer ions through the apertures in the ring electrodes or other electrodes. The travelling DC voltage waves applied to adjacent stacked ring ion guides or other ion guides may be arranged to run (or transmit ions) in opposite directions.

According to an embodiment ions may be arranged to travel forwards or in a first direction through a first stacked ring ion guide or other ion guide before being transferred into a second stacked ring ion guide or other ion guide. The ions may then pass back through the second stacked ring ion guide or other ion guide in a second direction which is preferably opposed or counter to the first direction. The ions may then be transferred into a third stacked ring ion guide or other ion guide so that the ions then travel forwards through the third stacked ring ion guide or other ion guide in the first direction. It is contemplated that further stacked ring ion guides or other ion guides may also be provided so that ions may be passed between a plurality of stacked ring ion guides or other ion guides. In this fashion the drift distance or effective drift path length of the ions can be greatly increased without unduly lengthening the device. It will be appreciated that in a commercial mass spectrometer it is important to reduce the overall footprint and size of the instrument as much as possible.

The length of the first ion guide section and/or the second ion guide section and/or the third ion guide section and/or optional further ion guide sections is preferably selected from the group consisting of: (i) <10 cm; (ii) 10-20 cm; (iii) 20-30 cm; (iv) 30-40 cm; (v) 40-50 cm; (vi) 50-60 cm; (vii) 60-70 cm; (viii) 70-80 cm; (ix) 80-90 cm; (x) 90-100 cm; (xi) 100-110 cm; (xii) 110-120 cm; (xiii) 120-130 cm; (xiv) 130-140 cm; (xv) 140-150 cm; (xvi) 150-160 cm; (xvii) 160-170 cm; (xviii) 170-180 cm; (xix) 180-190 cm; (xx) 190-200 cm; (xxi) 200-210 cm; (xxii) 210-220 cm; (xxiii) 220-230 cm; (xxiv) 230-240 cm; (xxv) 240-250 cm; (xxvi) 250-260 cm; (xxvii) 260-270 cm; (xxviii) 270-280 cm; (xxix) 280-290 cm; (ma) 290-300 cm; (xxxi) 300-310 cm; (xxxii) 310-320 cm; (xxxiii) 320-330 cm; (xxxiv) 330-340 cm; (xxxv) 340-350 cm; (xxxvi) 350-360 cm; (xxxvii) 360-370 cm; (xxxviii) 370-380 cm; (xxxix) 380-390 cm; (xl) 390-400 cm; (xli) 400-410 cm; (xlii) 410-420 cm; (xliii) 420-430 cm; (xliv) 430-440 cm; (xlv) 440-450 cm; (xlvi) 450-460 cm; (xlvii) 460-470 cm; (xlviii) 470-480 cm; (xlix) 480-490 cm; (l) 490-500 cm; and (li) >500 cm.

According to an embodiment the ion guide further comprises a device arranged and adapted to supply an AC or RF voltage to the electrodes comprising the ion guide and preferably the electrodes comprising the first ion guide section and/or the second ion guide section and/or the third ion guide section and/or further ion guide sections. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak. The amplitude of the AC or RF voltage applied to one or more intermediate ion guide sections is preferably greater than the amplitude of the AC or RF voltage applied to the first and/or the last ion guide sections.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

According to an embodiment the ion guide may comprise a device arranged and adapted to maintain a DC voltage or potential gradient along at least 5%, 10%, 15%, 20%, 25%, 30%, 35%, 40%, 45%, 50%, 55%, 60%, 65%, 70%, 75%, 80%, 85%, 90%, 95% or 100% of the length of the ion guide and preferably the length of the first ion guide section and/or the second ion guide section and/or the third ion guide section and/or further ion guide sections in order to urge, force, drive or propel ions through the ion guide and preferably the first ion guide section and/or the second ion guide section and/or the third ion guide section and/or further ion guide sections.

According to an embodiment the ion guide and preferably the first ion guide section and/or the second ion guide section and/or the third ion guide section and/or further ion guide sections may comprise an ion entrance port and an ion exit port and wherein, in use, a non-zero DC voltage or potential gradient is maintained between the ion entrance port or an entrance region of the ion guide (and preferably the first ion guide section and/or the second ion guide section and/or the third ion guide section and/or further ion guide sections) and the ion exit port or an exit region of the ion guide (and preferably the first ion guide section and/or the second ion guide section and/or the third ion guide section and/or further ion guide sections), wherein the non-zero DC voltage or potential gradient is arranged to urge, force, drive or propel ions through the ion guide (and preferably the first ion guide section and/or the second ion guide section and/or the third ion guide section and/or further ion guide sections) from the ion entrance port to the ion exit port.

The ion guide and preferably the first ion guide section and/or the second ion guide section and/or the third ion guide section and/or further ion guide sections preferably further comprise transient DC voltage means arranged and adapted to apply one or more transient DC voltages or potentials or one or more transient DC voltage or potential waveforms to at least some of the plurality of electrodes and preferably the first ion guide section and/or the second ion guide section and/or the third ion guide section and/or further ion guide sections in order to urge, force, drive or propel at least some ions along at least 5%, 10%, 15%, 20%, 25%, 30%, 35%, 40%, 45%, 50%, 55%, 60%, 65%, 70%, 75%, 80%, 85%, 90%, 95% or 100% of the length of the ion guide and preferably the first ion guide section and/or the second ion guide section and/or the third ion guide section and/or further ion guide sections.

According to an embodiment the ion guide and preferably the first ion guide section and/or the second ion guide section and/or the third ion guide section and/or further ion guide sections may comprise means arranged and adapted to vary, increase or decrease the amplitude of the one or more transient DC voltages or potentials or the one or more transient DC voltage or potential waveforms with time or wherein the amplitude of the one or more transient DC voltages or potentials or the one or more transient DC voltage or potential waveforms may be ramped, stepped, scanned or varied linearly or non-linearly with time.

In a mode of operation the one or more transient DC voltages or potentials or the one or more transient DC voltage or potential waveforms may be translated or applied along the length of the ion guide and preferably the first ion guide section and/or the second ion guide section and/or the third ion guide section and/or further ion guide sections at a velocity selected from the group consisting of: (i) <100 m/s; (ii) 100-200 m/s; (iii) 200-300 m/s; (iv) 300-400 m/s; (v) 400-500 m/s; (vi) 500-600 m/s; (vii) 600-700 m/s; (viii) 700-800 m/s; (ix) 800-900 m/s; (x) 900-1000 m/s; (xi) 1000-1100 m/s; (xii) 1100-1200 m/s; (xiii) 1200-1300 m/s; (xiv) 1300-1400 m/s; (xv) 1400-1500 m/s; (xvi) 1500-1600 m/s; (xvii) 1600-1700 m/s; (xviii) 1700-1800 m/s; (xix) 1800-1900 m/s; (xx) 1900-2000 m/s; (xxi) 2000-2100 m/s; (xxii) 2100-2200 m/s; (xxiii) 2200-2300 m/s; (xxiv) 2300-2400 m/s; (xxv) 2400-2500 m/s; (xxvi) 2500-2600 m/s; (xxvii) 2600-2700 m/s; (xxviii) 2700-2800 m/s; (xxix) 2800-2900 m/s; (xxx) 2900-3000 m/s; and (xxxi) >3000 m/s. According to an embodiment the velocity at which the one or more transient DC voltage or potential waveforms are preferably translated or applied along the length of the ion guide and preferably the first ion guide section and/or the second ion guide section and/or the third ion guide section and/or further ion guide sections may be varied, increased or decreased.

According to an embodiment an entrance region and/or a central region and/or an exit region of the ion guide and preferably the first ion guide section and/or the second ion guide section and/or the third ion guide section and/or further ion guide sections is preferably maintained in use at a pressure selected from the group consisting of: (i) >100 mbar; (ii) >10 mbar; (iii) >1 mbar; (iv) >0.1 mbar; (v) >$10^2$ mbar; (vi) >$10^{-3}$ mbar; (vii) >$10^{-4}$ mbar; (viii) >$10^{-5}$ mbar; (ix) >$10^{-6}$ mbar; (x) <100 mbar; (xi) <10 mbar; (xii) <1 mbar; (xiii) <0.1 mbar; (xiv) <$10^{-2}$ mbar; (xv) <$10^{-3}$ mbar; (xvi) <$10^{-4}$ mbar; (xvii) <$10^{-5}$ mbar; (xviii) <$10^{-6}$ mbar; (xix) 10-100 mbar; (xx) 1-10 mbar; (xxi) 0.1-1 mbar; (xxii) $10^{-2}$ to $10^{-1}$ mbar; (xxiii) $10^{-3}$ to $10^{-2}$ mbar; (xxiv) $10^{-4}$ to $10^{-3}$ mbar; and (xxv) $10^{-5}$ to $10^{-4}$ mbar.

The pressure of one or more intermediate ion guide sections is preferably arranged to be greater than the pressure of the first and/or last ion guide sections.

According to an embodiment the ion guide and preferably the first ion guide section and/or the second ion guide section and/or the third ion guide section and/or further ion guide sections may be supplied with a gas selected from the group consisting of: (i) xenon; (ii) uranium hexafluoride ("$UF_6$"); (iii) isobutane ("$C_4H_{10}$"); (iv) argon; (v) krypton; (vi) perfluoropropane ("$C_3F_8$"); (vii) hexafluoroethane ("$C_2F_6$"); (viii) hexane ("$C_6H_{14}$"); (ix) benzene ("$C_6H_6$"); (x) carbon tetrachloride ("$CCl_4$"); (xi) iodomethane ("$CH_3I$"); (xii) diiodomethane ("$CH_2I_2$"); (xiii) carbon dioxide ("$CO_2$"); (xiv) nitrogen dioxide ("$NO_2$"); (xv) sulphur dioxide ("$SO_2$"); (xvi) phosphorus trifluoride ("$PF_3$"); (xvii) disulphur decafluoride ("$S_2F_{10}$"); (xviii) nitrogen; (xix) air; (xx) methane; and (xxi) carbon dioxide. The gas may be arranged to flow in the same direction as ion travel within one or more ion guide sections or more preferably the gas may be arranged to flow counter to the direction of ion travel within one or more ion guide sections.

In a less preferred mode of operation ions may be transmitted along and through the ion guide and preferably the first ion guide section and/or the second ion guide section and/or the third ion guide section and/or further ion guide sections without substantially being separated within the ion guide according to their ion mobility or rate of change of ion mobility with electric field strength.

According to an embodiment the ion guide and preferably the first ion guide section and/or the second ion guide section and/or the third ion guide section and/or further ion guide sections may further comprise AC or RF voltage means arranged and adapted to apply two or more phase-shifted AC or RF voltages to electrodes forming at least part of the ion guide and preferably the first ion guide section and/or the second ion guide section and/or the third ion guide section and/or further ion guide sections in order to urge, force, drive or propel at least some ions along at least 5%, 10%, 15%, 20%, 25%, 30%, 35%, 40%, 45%, 50%, 55%, 60%, 65%, 70%, 75%, 80%, 85%, 90%, 95% or 100% of the length of the ion guide and preferably the first ion guide section and/or the second ion guide section and/or the third ion guide section and/or further ion guide sections.

According to an embodiment in a mode of operation ions are accelerated within the ion guide and preferably the first ion guide section and/or the second ion guide section and/or the third ion guide section and/or further ion guide sections so that they substantially achieve a terminal velocity.

According to an embodiment in a mode of operation singly charged ions having a mass to charge ratio in the range of 1-100, 100-200, 200-300, 300-400, 400-500, 500-600, 600-700, 700-800, 800-900, 900-1000 or >1000 preferably have a drift or transit time through the ion guide and preferably the first ion guide section and/or the second ion guide section and/or the third ion guide section and/or further ion guide sections in the range: (i) 0-1 ms; (ii) 1-2 ms; (iii) 2-3 ms; (iv) 3-4 ms; (v) 4-5 ms; (vi) 5-6 ms; (vii) 6-7 ms; (viii) 7-8 ms; (ix) 8-9 ms; (x) 9-10 ms; (xi) 10-11 ms; (xii) 11-12 ms; (xiii) 12-13 ms; (xiv) 13-14 ms; (xv) 14-15 ms; (xvi) 15-16 ms; (xvii) 16-17 ms; (xviii) 17-18 ms; (xix) 18-19 ms; (xx) 19-20 ms; (xxi) 20-21 ms; (xxii) 21-22 ms; (xxiii) 22-23 ms; (xxiv) 23-24 ms; (xxv) 24-25 ms; (xxvi) 25-26 ms; (xxvii) 26-27 ms; (xxviii) 27-28 ms; (xxix) 28-29 ms; (xxx) 29-30 ms; (xxxi) 30-35 ms; (xxxii) 35-40 ms; (xxxiii) 40-45 ms; (xxxiv) 45-50 ms; (xxxv) 50-55 ms; (xxxvi) 55-60 ms; (xxxvii) 60-65 ms; (xxxviii) 65-70 ms; (mix) 70-75 ms; (xl) 75-80 ms; (xli) 80-85 ms; (xlii) 85-90 ms; (xliii) 90-95 ms; (xliv) 95-100 ms; and (xlv) >100 ms.

According to an embodiment in a mode of operation ions may be collisionally cooled and/or thermalised by collisions with a gas within the ion guide and preferably within the first ion guide section and/or the second ion guide section and/or the third ion guide section and/or further ion guide sections.

According to another aspect of the present invention there is provided an ion mobility separator or ion mobility spectrometer comprising an ion guide as described above and wherein ions are arranged and adapted to be separated within the ion guide according to their ion mobility or their rate of change of ion mobility with electric field strength.

According to another aspect of the present invention there is provided a collision, reaction or fragmentation device comprising an ion guide as described above. The ion guide preferably forms part of a collision, reaction or fragmentation device selected from the group consisting of: (i) a Collisional Induced Dissociation ("CID") fragmentation device; (ii) a Surface Induced Dissociation ("SID")fragmentation device; (iii) an Electron Transfer Dissociation fragmentation device; (iv) an Electron Capture Dissociation fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an ion-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

According to another aspect of the present invention there is provided a mass spectrometer further comprising an ion guide as described above.

According to another aspect of the present invention there is provided a mass spectrometer further comprising an ion mobility separator or an ion mobility spectrometer as described above.

According to another aspect of the present invention there is provided a mass spectrometer further comprising a collision, fragmentation or reaction device as described above.

According to a preferred embodiment a compact, relatively high resolution and relatively high transmission low field ion mobility separator is preferably provided. The preferred ion mobility separator may be incorporated into a hybrid ion mobility-mass spectrometer arrangement.

According to the preferred embodiment the drift length of the preferred ion mobility spectrometer or separator is preferably increased by constraining ions into taking a tortuous path through the ion mobility spectrometer or separator. The overall physical dimensions of the preferred device are preferably considerably reduced when compared to a conventional ion mobility separator comprising a longitudinal drift tube having a comparable effective drift length.

According to an embodiment the mass spectrometer may comprise one or more ion sources selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) a sub-atmospheric pressure Electrospray ionisation ion source; and (xxii) a Direct Analysis in Real Time ("DART") ion source.

The mass spectrometer may comprise one or more continuous or pulsed ion sources.

The mass spectrometer may comprise one or more ion guides.

According to an embodiment the mass spectrometer may further comprise one or more further ion mobility separation devices and/or one or more Field Asymmetric Ion Mobility Spectrometer devices.

The mass spectrometer may comprise one or more ion traps or one or more ion trapping regions.

According to an embodiment the mass spectrometer may further comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device. The collision, fragmentation or reaction cell may be arranged upstream and/or downstream of the preferred ion mobility spectrometer or separator or ion guide.

According to an embodiment the mass spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or Orbitrap® mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

According to an embodiment the mass spectrometer may further comprise one or more energy analysers or electrostatic energy analysers.

According to an embodiment the mass spectrometer may further comprise one or more ion detectors.

According to an embodiment the mass spectrometer may further comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wein filter.

According to an embodiment the mass spectrometer may further comprise a device or ion gate for pulsing ions.

According to an embodiment the mass spectrometer may further comprise a device for converting a substantially continuous ion beam into a pulsed ion beam.

According to an embodiment the mass spectrometer may further comprise a C-trap and a mass analyser comprising an outer barrel-like electrode and a coaxial inner spindle-like electrode. In a first mode of operation ions may be transmitted to the C-trap and are then injected into the mass analyser. In a second mode of operation ions may be transmitted to the C-trap and then to a collision cell or Electron Transfer Dissociation device wherein at least some ions are fragmented into fragment ions, and wherein the fragment ions are then transmitted to the C-trap before being injected into the mass analyser.

According to an embodiment the mass spectrometer may comprise a stacked ring ion guide comprising a plurality of electrodes each having an aperture through which ions are transmitted in use and wherein the spacing of the electrodes increases along the length of the ion path. The apertures in the electrodes in an upstream section of the ion guide preferably have a first diameter and the apertures in the electrodes in a downstream section of the ion guide preferably have a second diameter which is preferably smaller than the first diameter. Opposite phases of an AC or RF voltage are preferably applied, in use, to successive electrodes.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENTS

Figure 1:
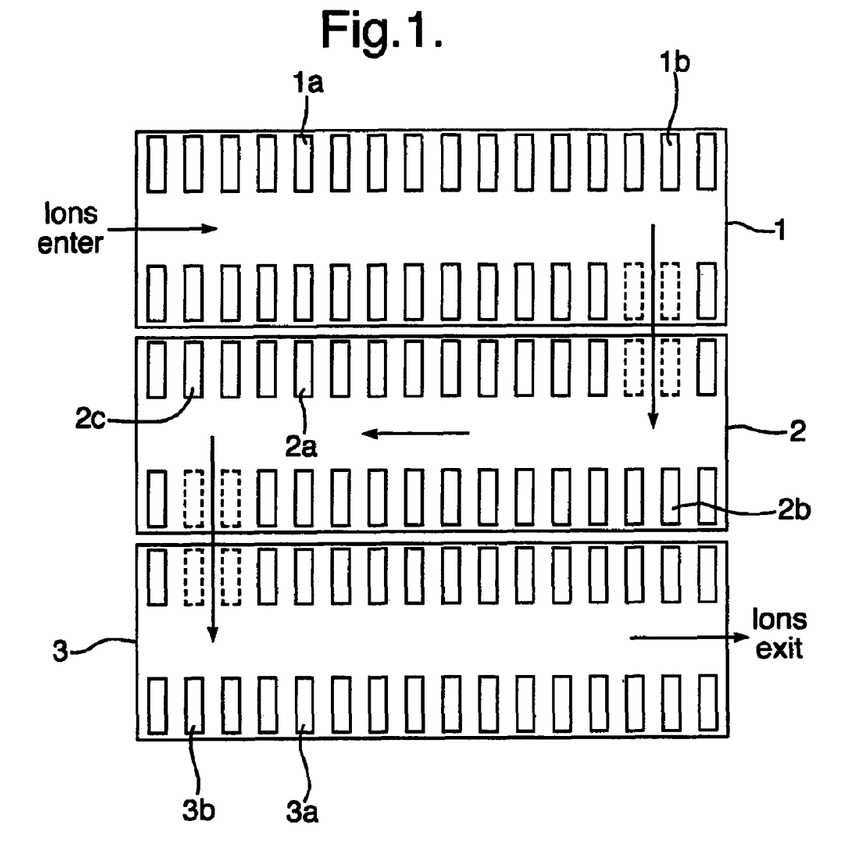
FIG. 1 shows a schematic of an ion guide array according to a preferred embodiment comprising three stacked ring ion guides wherein ions are ejected radially from one stacked ring ion guide to another.

A preferred embodiment of the present invention will now be described with reference to FIG. 1. FIG. 1 shows an ion guide array comprising three stacked ring ion guides 1,2,3. Ions are arranged to enter a first stacked ring ion guide 1 comprising a plurality of ring electrodes 1a each having an aperture through which ions are transmitted. Ions are propelled along the length of the first ion guide 1 by applying a DC travelling wave or one or more transient DC voltages or potentials to the electrodes 1a comprising the first ion guide 1.

Ions are therefore preferably translated to an end region of the first ion guide 1. A transfer section is preferably arranged at the end region of the first ion guide 1 and preferably comprises one or more ring electrodes 1b which have been modified so that a radial aperture or cut-out is provided in the ring electrodes 1b in the transfer section. In the particular example shown in FIG. 1 two ring electrodes 1b,2b in each stacked ring ion guide 1,2 are provided with a radial aperture or cut-out.

According to a particularly preferred aspect of the present invention ions may be transferred from the first ion guide section 1 into a second ion guide section 2 by passing radially or substantially radially through the aperture or radial cut-out provided in the ring electrodes 1b,2b which effectively form the transfer section between the two ion guide sections 1,2.

A DC bias is preferably maintained at least between the end region of the first ion guide 1 and the entrance region of the second ion guide 2 in order to urge ions from the first ion guide section 1 into the second ion guide section 2. Ions are therefore transferred radially from the first stacked ring ion guide 1 into the second stacked ring ion guide 2.

Ions are preferably propelled through the second stacked ring ion guide 2 by a DC travelling wave or transient DC voltage or potential in the reverse direction to the direction of travel of ions through the first ion guide 1. At the other end of the second stacked ring ion guide 2 the ions are then preferably arranged to pass radially from the second ion guide 2 through into a third stacked ring ion guide 3. The ions are then preferably propelled along and through the third ion guide 3 by a DC travelling wave or transient DC voltage or potential. The ions preferably exit at the end of the third stacked ring ion guide 3.

A particular advantage of the ion guide array as illustrated in FIG. 1 is that the overall ion guide has approximately three times the effective drift distance or length compared to a conventional ion tunnel ion guide comprising a single row of ring electrodes.

Three stacked ring ion guides 1,2,3 are shown in FIG. 1 merely as an example and it will be appreciated that further embodiments are contemplated wherein a different number of stacked ring ion guides in other ion guides may be provided. For example, the ion guide array may comprise just two ion guide sections or may comprise four, five, six, seven, eight, nine, ten or more than ten ion guide sections.

Figure 2:
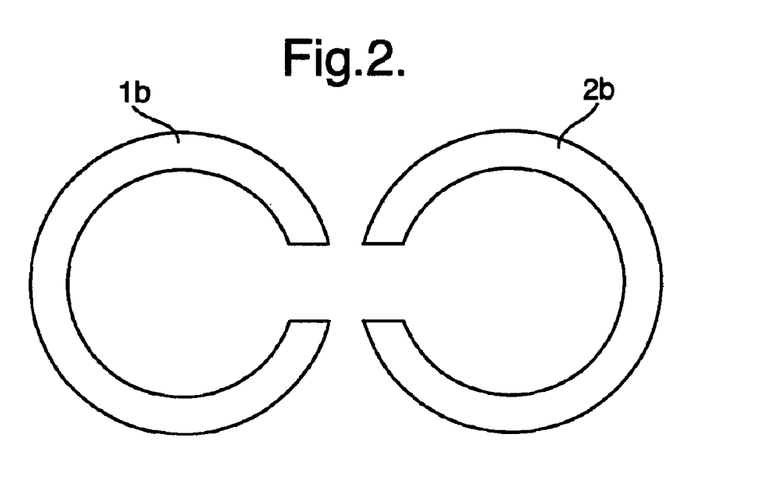
FIG. 2 shows a cross-sectional view of two adjacent stacked ring ion guide ring electrodes at the interface or transfer section between two adjacent stacked ring ion guides and shows that a radial aperture is preferably provided in the ring electrodes for ion transfer between the two adjacent stacked ring ion guides.

FIG. 2 shows two radially adjacent ring electrodes 1b,2b each having a radial aperture. One of the ring electrodes 1b is provided at an end region of the first ion guide section 1 and the other ring electrode 2b is provided at an entrance region of the second ion guide section 2. The two ring electrodes 1b,2b preferably form part of a transfer section between the two ion guide sections 1,2. The two adjacent stacked ring ion guide rings 1b,2b having aligned radial apertures preferably enable ions to transfer radially between the two adjacent stacked ring ion guides 1,2. According to the preferred embodiment this transfer may be effected or assisted by maintaining a DC bias voltage between the two adjacent stacked ring ion guides 1,2. According to other embodiments other methods may be used in order to urge ions from one ion guide to an adjacent ion guide. For example, a DC travelling wave or DC transient voltage or potential may be used or applied to electrodes in the transfer section between the two ion guides.

Figure 3:
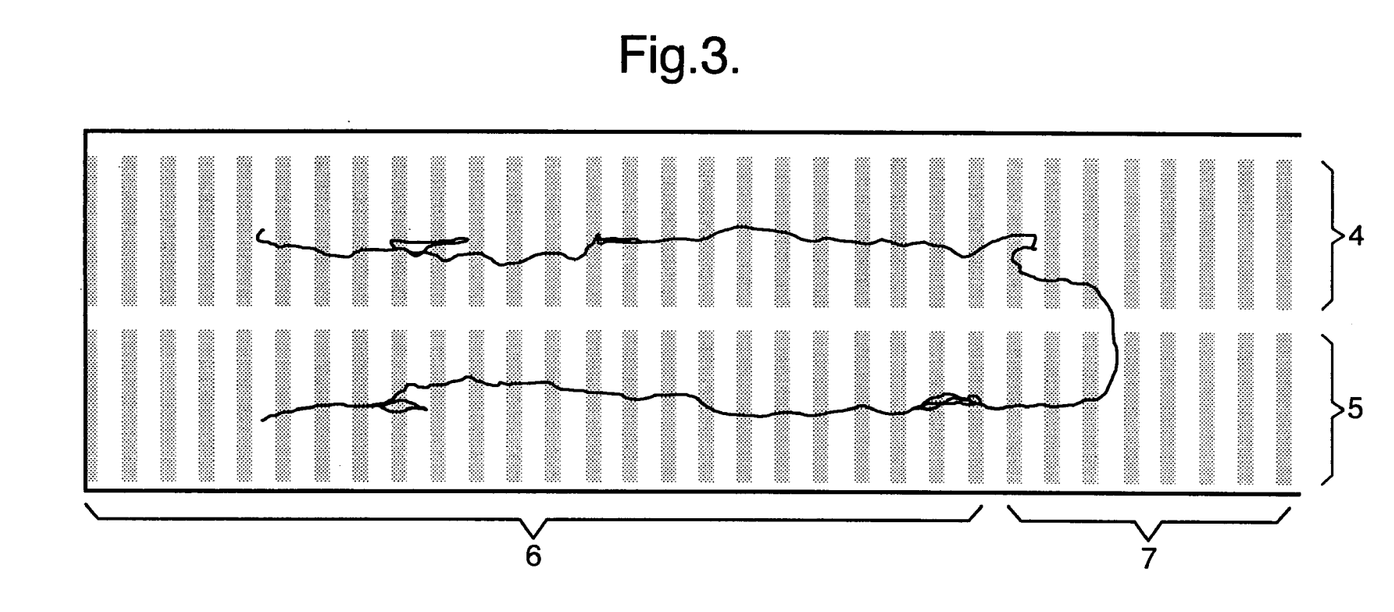
FIG. 3 shows a SIMION® simulation of an ion transferring between two adjacent stacked ring ion guides according to an embodiment of the present invention.

FIG. 3 shows the result of a SIMION® simulation and shows an ion path across the transfer region between two adjacent stacked ring ion guides 4,5. In this model the transfer region comprising electrodes with radial apertures comprises eight electrodes 7. The remaining electrodes comprise stacked ring ion guide electrode plates 6 which form a closed loop. A 5V DC bias is applied or maintained between the stacked ring ion guides 4,5 in the example shown in FIG. 3. The ion is modelled as being created in the upper stacked ring ion guide 4 and is then propelled to the right by a DC travelling wave or transient DC voltage or potential to the transfer region between the two ion guides 4,5. The ion is then rapidly transferred into the lower stacked ring ion guide 5. The ion is then propelled in the opposite direction by a DC travelling wave or DC transient voltage or potential.

In the simulation shown in FIG. 3 the RF potential applied to the electrodes was modelled as being 300 Vp-p RF at 2.7 MHz. The background gas was modelled as comprising 0.4 torr (0.5 mbar) Nitrogen. A 5V DC bias was maintained between the two stacked ring ion guides 4,5 with a four repeat 6V 300 m/s travelling wave pulse being applied to the electrodes. According to an embodiment these parameters may vary as for a normal ion mobility spectrometer or separator stacked ring ion guide cell e.g. up to a few torr (mbar) in gas pressure and a few tens of volts on the travelling wave pulse. The DC bias preferably ranges from a few volts up to a few tens of volts.

Figure 4A:
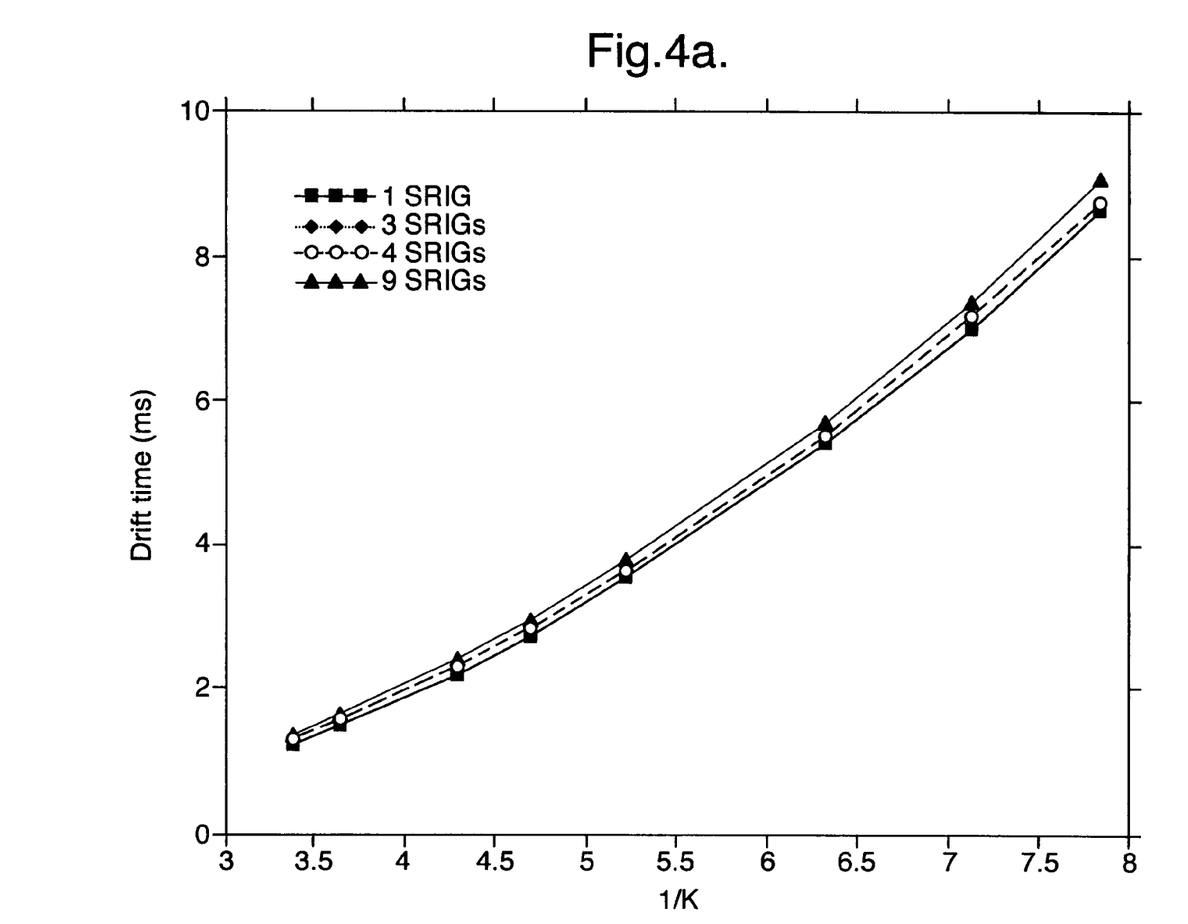
FIG. 4A shows the results of a SIMION® simulation wherein the scaled mean drift time is plotted for a range of ions in different ion guide arrays comprising one, three, four and nine stacked ring ion guides
Figure 4B:
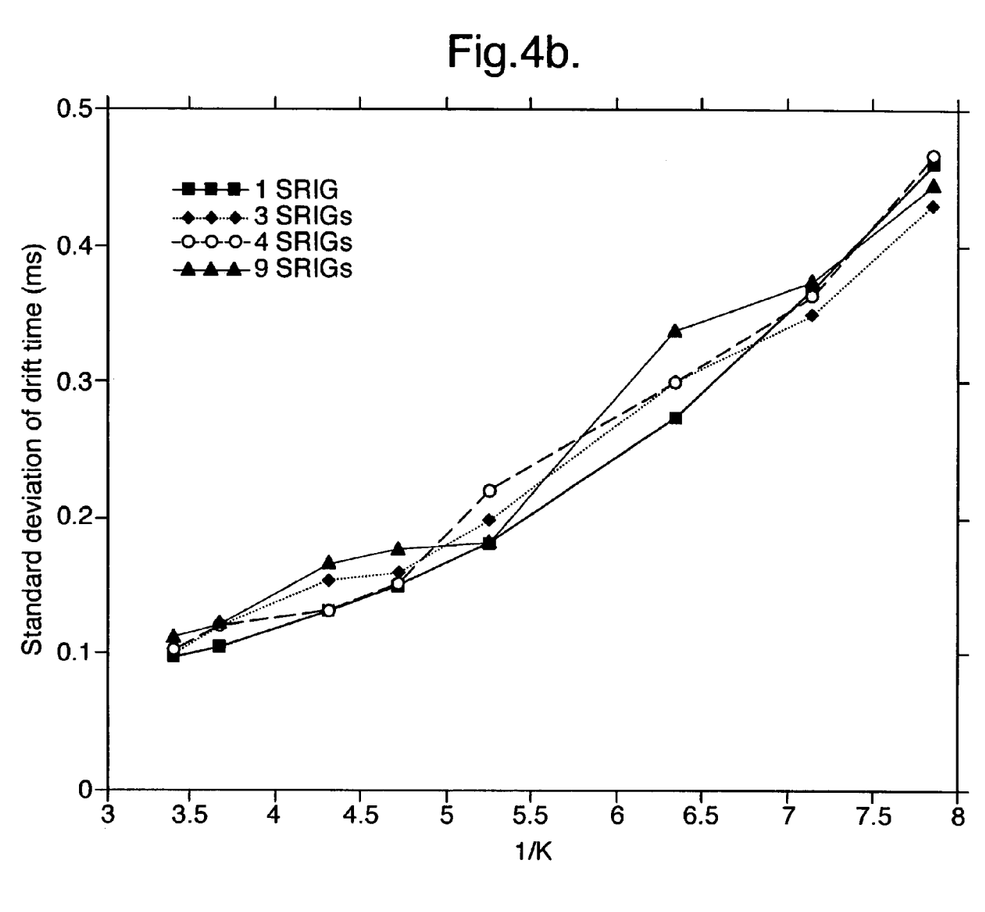
FIG. 4B shows the result of a SIMION® simulation wherein the standard deviation of the drift times is plotted for a range of ions in different ion guide arrays comprising one, three, four and nine stacked ring ion guides.

FIG. 4A shows mean drift times from SIMION® calculations for different ion guide arrays comprising one, three, four and nine stacked ring ion guides. FIG. 4B shows the corresponding standard deviation of the drift times. The drift times are scaled linearly by the number of stacked ring ion guides since it is expected that the drift time will be linearly related to the drift distance. It is apparent that this is indeed the case with all four scaled curves lying on a single line. The standard deviation is scaled by the square root of the number of stacked ring ion guides (since for a linear drift cell it is expected that the standard deviation will scale by the square root of the drift distance). Again it can be seen that the scaled standard deviations for all four arrangements lie on the same curve.

These results demonstrate that the ion mobility spectrometer or separator performance of the stacked ring ion guide system is comparable to that of a linear stacked ring ion guide having the same total or overall path length. Therefore, it is expected that the resolution of an ion guide array comprising a plurality of stacked ring ion guides will scale by the square root of the path length.

Further embodiments are contemplated wherein different numbers of stacked ring ion guides may be combined in this method. According to an embodiment different spatial configuration of stacked ring ion guides are also contemplated, e.g. vertical/horizontal stacks and 2D arrays.

According to an embodiment ions may enter and exit an ion guide array according to the preferred embodiment in different axial directions. According to another embodiment ions may be re-circulated and may pass through the sequence of stacked ring ion guides more than once.

Although the preferred method of propulsion of ions along the stacked ring ion guides is a DC travelling wave, other embodiments are contemplated wherein other different propulsion methods may be used including a constant axial DC potential difference.

According to an embodiment the method of ion transfer between adjacent stacked ring ion guides may comprise different transfer mechanisms rather than solely a DC bias potential.

According to an embodiment differing ion paths may be implemented in the same physical device by means of voltage switching.

Other less preferred embodiments are contemplated wherein the ion guides may comprise a multiple rod set or axially segmented multipole rod set. A further embodiment is also contemplated wherein the ion guide may comprise a plurality of plate electrodes arranged generally in the plane of ion travel. Opposite phases of an AC or RF voltage are applied to adjacent plate electrodes.

A further embodiment of the present invention is contemplated wherein the preferred ion guide comprises a plurality of ion guide sections. The pressure or effective pressure within the first or input and/or the last or output ion guide sections is preferably lower than the pressure or effective pressure within one or more intermediate ion guide sections particularly when the ion guide is used as an ion mobility separator or spectrometer. For example, according to an embodiment the first or input and/or the last or output ion guide sections may be maintained at a relatively low pressure to enable efficient coupling to other ion optical components such as an ion guide, mass filter or mass analyser and hence the first or input and/or the last or output ion guide sections may be maintained at a pressure of $10^{-5}$ mbar whereas one or more intermediate ion guide sections may be maintained at a much higher pressure, for example 0.5-5 mbar, to ensure adequate ion mobility separation is performed at least within the one or more intermediate ion guide sections. According to another embodiment the first or input and/or the last or output ion guide sections may be maintained at a relatively high pressure e.g. 0.1-1 mbar and one or more intermediate ion guide sections may be maintained at an even higher pressure e.g. in the range 1-100 mbar.

In addition to maintaining one or more intermediate ion guide sections at a higher pressure relative to the first or input and/or the last or output ion guide sections, further embodiments are contemplated wherein one or more parameters which effect the radial confinement of ions within the preferred ion guide are increased for the higher pressure intermediate ion guide sections. For example, according to an embodiment the amplitude of the RF voltage applied to the electrodes forming one or more intermediate ion guide sections for radial RF confinement of ions within the ion guide section may be higher than the amplitude of the RF voltage applied to the electrodes forming the first or input and/or the last or output ion guide sections. For example, the RF voltage applied to the first or input and/or the last or output ion guide sections may have an amplitude of 100-200 $V_{0\text{-peak}}$ whereas the RF voltage applied to one or more intermediate ion guide sections may be arranged to have an amplitude of 200-1000 $V_{0\text{-peak}}$. Embodiments are contemplated wherein the amplitude of the RF voltage applied to one or more of the intermediate ion guide sections may be of an order x2 or x3 greater than the amplitude of the RF voltage applied to the first or input and/or the last or output ion guide sections. Less preferred embodiments are also contemplated wherein the RF voltage applied to one or more intermediate ion guide sections may have a lower frequency than the RF voltage applied to the first or input and/or the last or output ion guide sections. According to other less preferred embodiments the internal diameter of the apertures formed in one or more intermediate ion guide sections may be arranged to be less than the internal diameter of the apertures formed in the first or input and/or the last or output ion guide sections. A further less preferred embodiment is contemplated wherein the axial spacing of the electrodes forming one or more intermediate ion guide sections is reduced relative to the axial spacing of the electrodes forming the first or input and/or the last or output ion guide sections.

Various different modes of operation are contemplated. According to a mode of operation ions may be transmitted through an ion guide section without being transmitted in a radial direction into a further ion guide section i.e. ions may by-pass the further ion guide sections. In a different mode of operation ions may be transmitted through a first ion guide section and the ions are then transmitted in a radial direction into a second ion guide section. For example, according to a mode of operation the ion guide may be switched between an ion guide mode of operation (wherein ions are transmitted through an ion guide section without being transferred radially into further ion guide sections) and an ion mobility mode of operation (wherein ions are transmitted radially into further ion guide sections and may then follow a generally tortuous path through the ion guide).

According to another related embodiment the ion guide can be operated so as to have a plurality of different ion exits. For example, ions having a relatively high ion mobility may be transferred between a relatively large number of ion guide sections and may emerge from the ion guide from, for example, the last ion guide section whereas ions having a relatively low ion mobility may be transferred between relatively fewer ion guide sections and may emerge from the ion guide from an intermediate ion guide section. According to this embodiment ions may be fractionated according to their ion mobility with different fractions of ions emerging from different exit regions of the ion guide or ion mobility spectrometer.

An embodiment of the present invention is contemplated wherein in a mode of operation ions may be passed through and around the ion guide so that the ions follow a closed loop path through the ion guide. An embodiment is contemplated wherein different ion guide sections are maintained at different static DC potentials and a DC travelling wave or transient DC voltage or potential is used to drive ions from the last ion guide section back around to the first ion guide section against an opposed DC potential. Alternatively, if the ions admitted into the ion guide are arranged to have a relatively small mass to charge ratio or ion mobility range then ions within the ion guide can be arranged to be present in just one or two ion guide sections at any particular instance in time. According to this embodiment the potential of the various ion guide sections can be continuously or otherwise altered so that ions may be caused to make one or more circuits of the ion guide. This embodiment is particularly suitable for high resolution ion mobility separation of ions having substantially similar mass to charge ratios or ion mobilities.

According to further embodiments a flow of neutral gas (e.g. nitrogen or argon) may be arranged to flow through the first or input ion guide section and/or one or more intermediate ion guide sections and/or the last or output ion guide section. According to an embodiment the flow of neutral gas may be arranged to flow in an opposed or counter-flow direction to the direction of transmission of ions. A counter-flow of neutral gas will have the effect of increasing the effective pressure within the ion guide section and hence improves the ion mobility resolution.

Although the present invention has been described with reference to preferred embodiments, it will be understood by those skilled in the art that various modifications may be made to the particular embodiments discussed above without departing from the scope of the invention as set forth in the accompanying claims.

The invention claimed is:
1. An ion guide comprising:
a first ion guide section comprising a first plurality of electrodes having at least one aperture through which ions are transmitted in use;
a second ion guide section comprising a second plurality of electrodes having at least one aperture through which ions are transmitted in use;

a first transfer section connecting said first ion guide section with said second ion guide section wherein ions are transmitted radially, in use, in said first transfer section from said first ion guide section into said second ion guide section, wherein said first and second ion guide sections comprise stacked ring ion guides and said first transfer section comprises one or more electrodes in said first ion guide section having a first radial aperture or cut-out and one or more electrodes in said second ion guide section having a second radial aperture or cut-out; and means for applying an AC or RF voltage to alternate ring electrodes of the stacked ring ion guides in order to confine ions radially within the first and second ion guide sections.

2. An ion guide as claimed in claim 1, wherein said first radial aperture or cut-out and said second radial aperture or cut-out are substantially aligned and wherein said first radial aperture or cut-out faces said second radial aperture or cut-out.

3. An ion guide as claimed in claim 1, further comprising a first device for urging ions from said first ion guide section into said second ion guide section via said first transfer section.

4. An ion guide as claimed in claim 3, wherein said first device comprises:
   (i) a device for maintaining a DC potential bias across said first transfer section so that ions are urged from said first ion guide section into said second ion guide section; or
   (ii) a device for applying one or more transient DC voltages or potentials or one or more transient DC voltage or potential waveforms to electrodes arranged in said first transfer section so that ions are urged from said first ion guide section into said second ion guide section.

5. An ion guide as claimed in claim 1, wherein ions are transmitted in use in a first direction through said first ion guide section and in a second direction through said second ion guide section, wherein either:
   (i) said first direction is substantially the same as said second direction; or
   (ii) said first direction is substantially different to or counter to said second direction.

6. An ion guide as claimed in claim 1, further comprising:
a first transient DC voltage means arranged and adapted to apply one or more transient DC voltages or potentials or one or more transient DC voltage or potential waveforms to at least some of said first plurality of electrodes in order to urge, force, drive or propel at least some ions along at least 5%, 10%, 15%, 20%, 25%, 30%, 35%, 40%, 45%, 50%, 55%, 60%, 65%, 70%, 75%, 80%, 85%, 90%, 95% or 100% of the length of said first ion guide section; and
a second transient DC voltage means arranged and adapted to apply one or more transient DC voltages or potentials or one or more transient DC voltage or potential waveforms to at least some of said second plurality of electrodes in order to urge, force, drive or propel at least some ions along at least 5%, 10%, 15%, 20%, 25%, 30%, 35%, 40%, 45%, 50%, 55%, 60%, 65%, 70%, 75%, 80%, 85%, 90%, 95% or 100% of the length of said second ion guide section.

7. An ion guide as claimed in claim 1, wherein said ion guide further comprises a third ion guide section comprising a third plurality of electrodes having at least one aperture through which ions are transmitted in use, and a second transfer section connecting said second ion guide section with said third ion guide section wherein ions are transmitted radially, in use, in said second transfer section from said second ion guide section into said third ion guide section.

8. An ion guide as claimed in claim 7, wherein said second transfer section comprises one or more electrodes in said second ion guide section having a third radial aperture or cut-out and one or more electrodes in said third ion guide section having a fourth radial aperture or cut-out.

9. An ion guide as claimed in claim 8, wherein said third radial aperture or cut-out and said fourth radial aperture or cut-out are substantially aligned and wherein said third radial aperture or cut-out faces said fourth radial aperture or cut-out.

10. An ion guide as claimed in claim 7, further comprising a second device for urging ions from said second ion guide section into said third ion guide section via said second transfer section.

11. An ion guide as claimed in claim 7, wherein ions are transmitted in use in a third direction through said third ion guide section and wherein either:
   (i) said third direction is substantially the same as said first direction or said second direction; or
   (ii) said third direction is substantially different to or counter to said first direction or said second direction.

12. An ion guide as claimed in claim 1, wherein in a first mode of operation ions are arranged to pass through said first ion guide section and exit said first ion guide section without being transmitted into said second ion guide section and wherein in a second mode of operation ions are arranged to pass through said first ion guide section and are transferred radially from said first ion guide section to said second ion guide section.

13. An ion guide as claimed in claim 1, further comprising a device for causing gas to flow through said first ion guide section or said second ion guide section or one or more further ion guide sections, wherein said gas is arranged to flow in a direction which is generally counter or opposed to the direction in which ions are transmitted through said first ion guide section or said second ion guide section or one or more further ion guide sections.

14. An ion mobility spectrometer or separator, a collision, fragmentation or reaction cell, or a mass spectrometer comprising an ion guide comprising:
   a first ion guide section comprising a first plurality of electrodes having at least one aperture through which ions are transmitted in use;
   a second ion guide section comprising a second plurality of electrodes having at least one aperture through which ions are transmitted in use;
   a first transfer section connecting said first ion guide section with said second ion guide section wherein ions are transmitted radially, in use, in said first transfer section from said first ion guide section into said second ion guide section, wherein said first and second ion guide sections comprise stacked ring ion guides and said first transfer section comprises one or more electrodes in said first ion guide section having a first radial aperture or cut-out and one or more electrodes in said second ion guide section having a second radial aperture or cut-out; and
   means for applying an AC or RF voltage to alternate ring electrodes of the stacked ring ion guides in order to confine ions radially within the first and second ion guide sections.

15. A method of guiding ions comprising:
   providing an ion guide comprising a first ion guide section comprising a first plurality of electrodes having at least one aperture through which ions are transmitted, a second ion guide section comprising a second plurality of electrodes having at least one aperture through which ions are transmitted and a first transfer section connecting said first ion guide section with said second ion guide section wherein said first and second ion guide sections comprise stacked ring ion guides and said first transfer section comprises one or more electrodes in said first ion guide section having a first radial aperture or cut-out and one or more electrodes in said second ion guide section having a second radial aperture or cut-out;

transmitting ions radially in said first transfer section from said first ion guide section into said second ion guide section; and applying an AC or RF voltage to alternate ring electrodes of the stacked ring ion guides to confine ions radially within the first and second ion guide sections.

* * * * *